(12) United States Patent
Austerlitz et al.

(10) Patent No.: US 10,586,081 B2
(45) Date of Patent: Mar. 10, 2020

(54) APPARATUS AND METHOD FOR STORING AND RETRIEVING OPTICAL SENSOR CALIBRATION DATA

(71) Applicant: Parker-Hannifin Corporation, Cleveland, OH (US)

(72) Inventors: Howard Austerlitz, Stony Brook, NY (US); Lewis Boyd, Bath (GB)

(73) Assignee: Parker-Hannifin Corporation, Cleveland, OH (US)

( * ) Notice: Subject to any disclaimer, the term of this patent is extended or adjusted under 35 U.S.C. 154(b) by 657 days.

(21) Appl. No.: 15/071,964

(22) Filed: Mar. 16, 2016

(65) Prior Publication Data

US 2016/0275982 A1    Sep. 22, 2016

Related U.S. Application Data

(60) Provisional application No. 62/134,627, filed on Mar. 18, 2015.

(51) Int. Cl.
  *G06K 7/00*     (2006.01)
  *G01D 5/353*    (2006.01)
  *G11C 13/04*    (2006.01)
  *G01N 33/22*    (2006.01)

(52) U.S. Cl.
  CPC .......... *G06K 7/00* (2013.01); *G01D 5/35316* (2013.01); *G01D 5/35367* (2013.01); *G11C 13/042* (2013.01); *G01N 33/22* (2013.01)

(58) Field of Classification Search
  CPC ..... G01D 5/35316; G01P 15/093; G06K 7/00
  See application file for complete search history.

(56) References Cited

U.S. PATENT DOCUMENTS

| 4,286,145 | A | 8/1981 | Palmer | |
|---|---|---|---|---|
| 5,956,447 | A | 9/1999 | Zel'Dovich et al. | |
| 7,212,705 | B2 * | 5/2007 | Shahar | G02B 6/125 385/24 |
| 2002/0041722 | A1 * | 4/2002 | Johnson | G01D 5/35383 385/12 |
| 2007/0014577 | A1 * | 1/2007 | Austerlitz | H04B 10/2503 398/140 |
| 2010/0313659 | A1 * | 12/2010 | Berg | G01P 15/093 73/514.26 |
| 2014/0063493 | A1 * | 3/2014 | Nash | G01D 5/35383 356/226 |

* cited by examiner

*Primary Examiner* — Sung H Pak
*Assistant Examiner* — Hoang Q Tran
(74) *Attorney, Agent, or Firm* — Renner, Otto, Boisselle & Sklar, LLP

(57) ABSTRACT

An optical storage device for storing data includes at least one optical waveguide for receiving an optical interrogation signal and providing a response to the optical interrogation signal and a plurality of optical elements arranged relative to the at least one optical waveguide. The plurality of optical elements are responsive to the optical interrogation signal provided through the at least one waveguide to return a prescribed data value through the at least one optical waveguide. The plurality of optical elements represent encoded data concerning a function of an optical sensor.

22 Claims, 6 Drawing Sheets

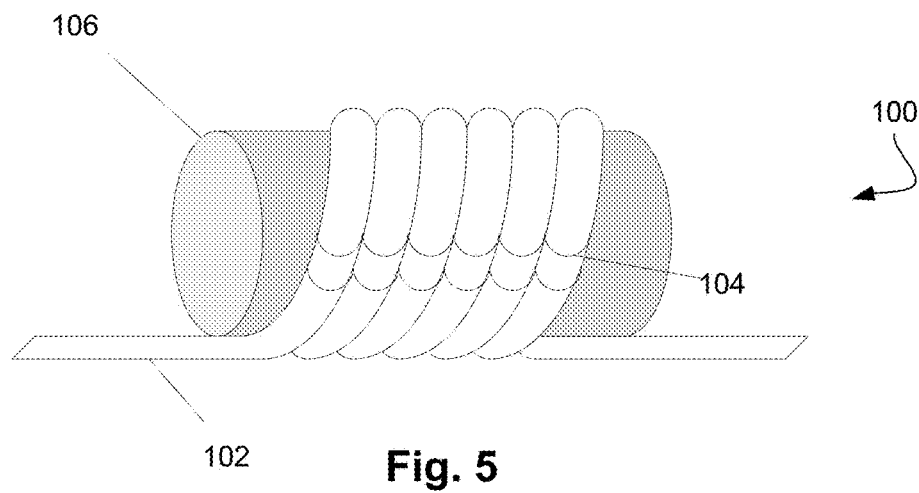
Fig. 5
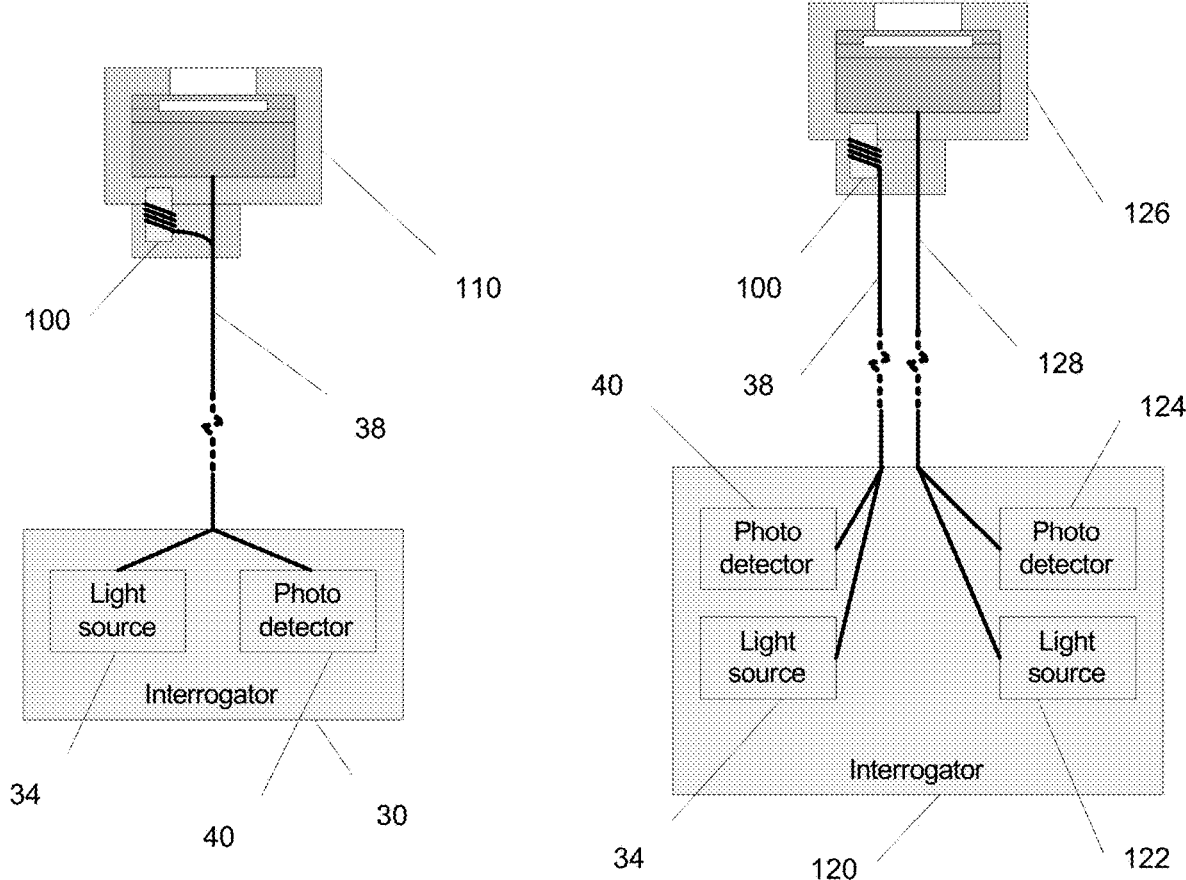
Fig. 6
Fig. 7

APPARATUS AND METHOD FOR STORING AND RETRIEVING OPTICAL SENSOR CALIBRATION DATA

RELATED APPLICATIONS

This application claims the benefit of U.S. Provisional Application No. 62/134,627 filed Mar. 18, 2015, which is incorporated herein by reference in its entirety.

FIELD OF THE INVENTION

The present invention relates to sensors and, more particularly, to a method and apparatus for optically storing and optically retrieving data for a sensor, such as calibration data, sensor serial number, or the like.

BACKGROUND

Use of highly accurate sensors almost certainly requires calibration data to be used in the associated electronics. These calibration data may reasonably be assumed to be different from one sensor to another due to manufacturing tolerances and other variations.

In aerospace applications, it is often a requirement for these data to be physically stored on the sensor itself, thereby enabling the data to be read automatically by the interfacing avionics. A benefit on such approach is that if the sensor is replaced, the system can read the new calibration data from the new sensor and continue to perform, meeting its accuracy requirements, with no additional manual process to associate the new sensor with its calibration data.

In systems using electronic sensors with embedded circuits, storing the calibration data is relatively simple and can be achieved using programmable devices such as erasable programmable read only memory (EPROM). However, where intrinsic safety and electromagnetic interference (EMI) considerations drive the use of optical sensors and fiber optic communication with the sensor, EPROM can no longer be used without reintroducing an electrical connection to the sensor, obviating the benefits of the optical device.

SUMMARY OF THE INVENTION

The present disclosure provides a means by which data, such as sensor calibration data, sensor serial number, or the like, can be encoded using an array of optical elements that can be read by the same or other opto-electronics device that interfaces with the sensor. In this manner, the data can be stored on and retrieved from the sensor in an intrinsically safe manner.

An optical read-only storage device in accordance with the present disclosure enables optically encoded digital data (e.g., 8 to 32 bits) to be read using a single optical fiber and a relatively low level of optical power (e.g., much less than 150 mW limits for intrinsic safety operation in explosive atmospheres or eye safety standards). The optical storage device is suitable for reading, for example, ID numbers or calibration data of sensing units located within an aircraft's fuel tank (such as densitometers, capacitance fuel level sensors, or any other in-tank sensors), or any device that requires data storage and retrieval in an intrinsically safe manner. The optical storage device does not require active optical or electronic components and may only require the small amount of energy supplied by an interrogation laser.

In accordance with one aspect of the present disclosure, optical data can be stored by utilizing a plurality of optical waveguides, such as a plurality of optical fibers, each coupled to a common interrogation port via a series of splitters or the like. Optical elements, such as optical reflectors and optical absorbers, can terminate each optical waveguide, where an optical reflector can be regarded as having a value of one and an optical absorber can be regarded as having a value of zero. Each optical waveguide may also include a delay element arranged between the optical element and the interrogation port, the delay element configured to delay the transfer of light. The plurality of optical elements can form a binary store and can be interrogated using time division multiplexing to obtain a binary value representative of a calibration value or other value.

In accordance with another aspect of the present disclosure, data may also be stored optically using Fiber Bragg Gratings (FBGs) formed within a single waveguide (e.g., within a single optical fiber). More particularly, a plurality of FBGs may be formed in a single waveguide, where each FBG is configured to reflect light at a specific peak wavelength that is different from other FBGs, while letting light of other wavelengths pass through the waveguide. In this regard, each FBG can represent a single digit of information. The data stored by the FBGs then can retrieved by wavelength division multiplexing.

According to one aspect of the disclosure, an optical storage device for storing data includes: at least one optical waveguide for receiving an optical interrogation signal and providing a response to the optical interrogation signal; and a plurality of optical elements arranged relative to the at least one optical waveguide and responsive to the optical interrogation signal provided through the at least one waveguide to return a prescribed data value through the at least one optical waveguide, wherein the plurality of optical elements represent encoded data concerning a function of an optical sensor.

Optionally, the optical storage device includes: an interrogation port for interrogating the optical storage device; a plurality of optical waveguides optically coupled to the interrogation port, each optical waveguide of the plurality of optical waveguides including a delay element operative to delay the transmission of optical data through a portion of the respective optical waveguide, wherein respective ones of the plurality of optical elements terminate respective ones of the plurality of optical waveguides in a prescribed arrangement to form a data sequence.

Optionally, the optical elements comprise i) optical reflectors and optical absorbers, or ii) polarization changing elements.

Optionally, the delay introduced by each respective delay element of the plurality of delay elements is different from other delay elements of the plurality of delay elements.

Optionally, each delay element of the plurality of delay elements is arranged optically between the interrogation port and the respective optical element.

Optionally, the optical storage device includes at least one optical splitter having an input port and a plurality of output ports, wherein the input port is coupled to the interrogation port and respective ones of the plurality of optical waveguides are coupled to respective ones of the plurality of output ports.

Optionally, the plurality of optical elements are spaced arranged within the at least one optical waveguide, each optical element of the plurality of optical elements spaced apart from other optical elements of the plurality of optical elements and configured to reflect light at a prescribed wavelength, wherein the prescribed wavelength for each respective optical element of the plurality of optical elements is different from one another.

Optionally, the array of optical elements comprise a plurality of Fiber Bragg Gratings (FBG) arranged serially in the optical fiber.

Optionally, the optical waveguide is arranged in a coil configuration.

Optionally, the optical waveguide is wrapped around a central core (e.g., a mandrel) to produce a coil-shape optical waveguide.

Optionally, the central core comprises a non-conductive material.

Optionally, the plurality of optical elements are written (e.g., etched) within the optical waveguide.

Optionally, the spacing between adjacent optical elements is between 10 centimeters and 100 centimeters.

Optionally, the plurality of optical elements are configured to provide partial reflections of the optical interrogation signal.

Optionally, the partial reflections comprise n different bands, where n is an integer greater than 1.

Optionally, the optical waveguide comprises an optical fiber.

Optionally the optical waveguide comprises a waveguide written directly into a planar optical structure According to another aspect of the present disclosure, an optical sensor system includes: an optical sensor, and the optical storage device described herein.

Optionally, the optical sensor system includes an interrogator communicatively coupled to the optical sensor via a first optical medium, and communicatively coupled to the optical storage device via a second optical medium.

Optionally, the first optical medium and the second optical medium are different from one another.

Optionally, the interrogator is configured to decode data received from the optical storage device based on time division multiplexing and time of flight calculations.

Optionally, the interrogator is configured to decode data received from the optical storage device based on one of time division multiplexing or wavelength division multiplexing.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

FIG. 5 is a schematic diagram of an exemplary optical storage device in accordance another embodiment of with the present disclosure.

FIG. 6 is a schematic diagram of an optical sensor that includes the optical storage device of FIG. 5, wherein the optical sensor and the optical storage device are coupled to an interrogator using a common optical medium.

FIG. 7 is a schematic diagram of an optical sensor that includes the optical storage device of FIG. 5, wherein the optical sensor and the optical storage device are coupled to an interrogator using different optical mediums.

DETAILED DESCRIPTION

Aspects of the present disclosure will now be described in the context of an optical sensor. It should be appreciated, however, that aspects of the disclosure are applicable to other applications in which a data storage and retrieval is required in an intrinsically safe manner.

An optical storage device in accordance with the present disclosure uses optical waveguides as a means for storing data. The optical storage device includes at least one optical waveguide, such as an optical fiber or the like, for receiving an optical interrogation signal from an interrogating device, and providing a response to the optical interrogation signal. As discussed in more detail below, the optical interrogation signal may be provided by a remotely located optical interrogator coupled to the optical storage device.

The optical storage device further includes a plurality of optical elements arranged relative to the at least one optical waveguide. The plurality of optical elements are responsive to the optical interrogation signal provided through the at least one waveguide to provide a prescribed data value. For example, each optical element may respond to the interrogation signal with a reflection of the interrogation signal (which can be interpreted as a value of one) or without providing a response to the interrogation signal (which can be interpreted as a value of zero), where each optical element is configured to represent at least a portion of the stored data. The plurality of optical elements, when taken as a combination, provide encoded data concerning an optical sensor and can be optically read by an interrogation device.

Figure 1A:
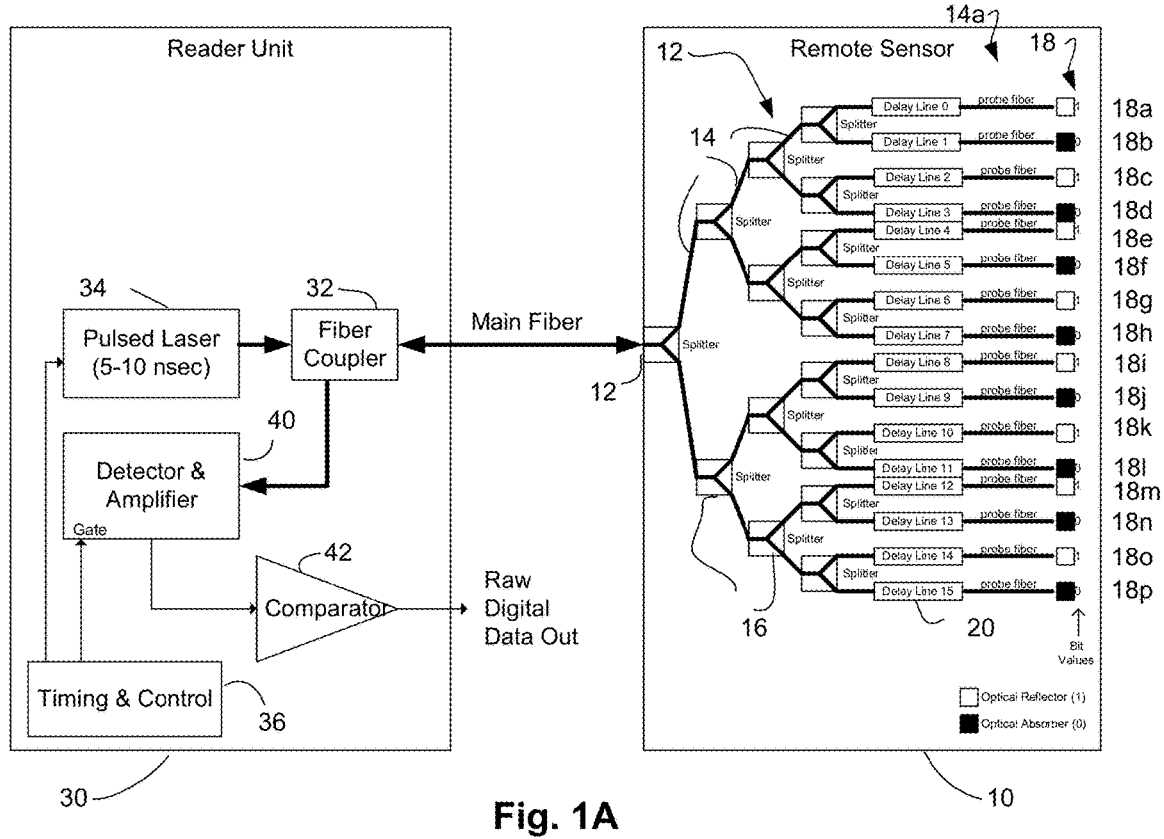
FIG. 1A is a block diagram of an exemplary optical storage device coupled to an interrogator in accordance an embodiment of the present disclosure.

Referring to FIG. 1, illustrated is a first embodiment of an optical storage device 10 in accordance with the present disclosure. The optical storage device 10 includes an interrogation port 12, which provides a means for connecting the optical storage device 10 to another device in order to read the data stored on the optical storage device 10. The optical storage device 10 also includes a plurality of individual optical waveguides 14, such as optical fibers or the like. The plurality of optical waveguides 14 are optically coupled to the interrogation port 12 via a series of optical splitters 16, thereby forming a passive array 14a of single waveguides 14.

For example, each splitter 16 may have an input port and a plurality of output ports. By forming series and parallel branches via the respective ports of the splitters 16, a number of waveguides 14 can be coupled to the interrogation port 12 as shown in FIG. 1. In the exemplary embodiment shown in FIG. 1, two-port splitters are employed. It will be appreciated, however, that any combination of a two-port, three-port, four-port, five-port, etc. splitters may be used depending on the requirements of the specific application.

The optical storage device 10 also includes a plurality of optical elements 18. In one embodiment, the optical elements 18 may be one of an optical reflector (which can represent a value of one) or an optical absorber (which can represent a value of zero), and can be formed by applying a light reflecting or light absorbing coating on the waveguide end. Respective ones of the plurality of optical elements 18 terminate respective ones of the plurality of optical waveguides 14 in a prescribed arrangement to form a data sequence (e.g., a series of binary bits that form a data word).

Each optical waveguide 14 also includes a serial delay element 20 operative to delay the transmission of optical data through a portion of the respective optical waveguide 14. In particular, each delay element 20 is arranged optically between the interrogation port 12 and the respective optical element 18. The delay elements 18 are configured to provide different delay times depending on which bit of a data word the respective waveguide represents. To implement a delay, the delay elements 20 may be embodied as waveguides (e.g., optical fibers) each having different lengths relative to other delay elements, thereby requiring that the light travel over longer distances. Since the light must travel over longer lengths, a delay is introduced. As described in more detail below, the data stored by the optical storage device 10 can be read using time division multiplexing (TDM) and time-of-flight techniques, which can be decoded by the interfacing opto-electronics. The basic concept for reading data from the optical storage device 10 is to transmit a narrow laser pulse (e.g., 5-10 nanoseconds) through the optical medium into a remote device, such as a sensor, that includes the optical storage device 10. In the optical storage device 10, the optical energy is divided into n-waveguides (for n-bits of data: e.g., 16 waveguides) using the splitters 16. Each waveguide line (or bit) passes through the delay element 20 that has a unique value having a multiple of the laser pulse width. For example, if the laser pulse is 10 nanoseconds wide, bit 0 can have a delay element 20 of 0 nanoseconds, bit 1 can have a delay element of 5 nanoseconds, bit 2 can have a delay element of 10 nanoseconds, . . . , bit 15 can have a delay element of 75 nanoseconds). The total differential delay is two times the delay element value, since the signal passes through the delay element twice. After the delay element, each waveguide 14 is terminated. If the waveguide end is terminated with an optical reflector it has a bit value of one. If the waveguide 14 is terminated with an optical absorber, it has a bit value of zero. Further, the first bit can be used as a reference bit for all subsequent measurements as discussed below with respect to another embodiment.

FIG. 1 also illustrates an exemplary interrogator 30 (also referred to as a reader or data reader) for reading data from the optical storage device 10. The interrogator 30 includes a coupler 32 for optically coupling to the interrogation port 12 of the optical storage device 10. An interrogation signal for interrogating the optical storage device 10 can be generated by a pulsed laser 34 optically coupled to the coupler 32, the laser 34 being under the control of timing and control circuitry 36. The pulsed interrogation signal is provided to the coupler 32 and then transmitted to the optical storage device 10 via an optical medium 38 (such as an optical fiber or the like) coupled between the coupler 32 and the interrogation port 12. The interrogation signal enters the interrogation port 12 and propagates through the array of waveguides 14, splitters 16, delay elements 20 and reaches the optical elements 18. Depending on the type of optical element 18 (reflector or absorber) a response may or may not be generated. The response (or lack thereof) propagates back toward the interrogation port 12 through the waveguides 14, delay elements 20, various splitters 16, where it exits the interrogation port 12 and is communicated to the interrogator 30 via the optical medium 38. The interrogator 30 receives the response signal via the coupler 32, where it then is provided to detector and amplifier circuitry 40 for decoding. The decoded data then is provided to comparator 42 to generate a raw digital output for use by other devices.

Figure 2:
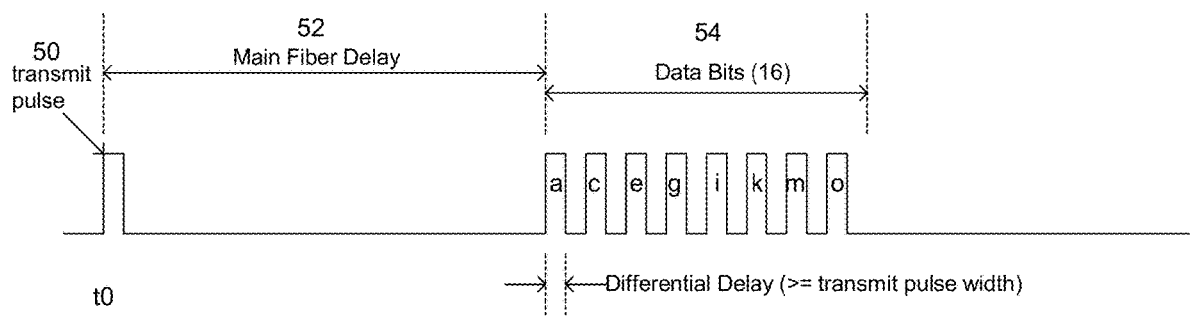
FIG. 2 is a timing diagram illustrating a timing sequence for reading data from the optical storage device in accordance with the present disclosure.

FIG. 2 illustrates an exemplary timing sequence for an interrogation signal 50 from the interrogator 30 through the optical storage device 10. More particularly, under the control of the timing and control circuitry 36 the laser 34 generates a short transmit pulse 50 (e.g., 10 nanosecond) at time $t_0$, which may be a square wave pulse. The transmit pulse 50 exits the coupler 32 and travels toward the optical storage device 10 via optical medium 38, which introduces a first delay time 52. The length of the first delay time is dependent on the length of the optical medium 38 between the interrogator 30 and the optical storage device 10.

Upon the transmit pulse 50 reaching the optical storage device 10, the signal propagates through the various waveguides 14, splitters 16 and delay elements 20 until it reaches respective ones of the optical elements 18. Due to the different delay times introduced by the different delay elements 20, the time at which the transmit pulse 50 arrives at the optical element 18a for the LSB is temporally before the time the transmit pulse 50 arrives at any of the other optical elements 18b-18p. Similarly, the time at which the transmit pulse 50 arrives at the optical element 18b is temporally before the time the transmit pulse 50 arrives at the optical elements 18c-18p, and so on.

Upon the transmit pulse 50 reaching the respective optical elements 18a-18p, the signal will either be reflected (representing a value of one) or absorbed (representing a value of zero). The reflected signal will propagate back through the delay elements 20, splitters 16 and waveguides 14 and exit the interrogation port 12 and travel back to the interrogator 30 via the optical medium 38, separated in time by two times the differential delay line values (typically, the laser pulse width, or higher). The waveform 54 illustrated in FIG. 2 represents the reflected signals from optical elements 18a, 18c, 183, 18g, 18i, 18k, 18m and 18o that is received by the interrogator 30 and processed to provide a digital value.

The timing and control circuitry 36 can know the time required for the transmit pulse 50 to make a round trip to each of the respective optical elements 18a-18p and, thus, can read the values from the optical storage device 10 at predetermined time intervals after the transmit pulse 50 is sent. Thus, for example, the timing and control circuitry 36 may know that at 60 nanoseconds after the transmit pulse 50 is sent a response can be expected from the LSB 18a, and 60 nanoseconds later a response can be expected from the next significant bit, and so on. If the detector detects a reflection signal at the specified interval, then this can be equated to a value of one, and if the detector does not detect a reflection at the specified interval, then this can be equated to a value of zero. The sequence of bits then can be assembled and decoded as a binary number representative, for example, of a calibration value or identifier of a sensor. The calibration value and/or identifier then can be used to scale data provided by the sensor and/or retrieve additional formation related to the sensor as described in more detail below.

Figure 1B:
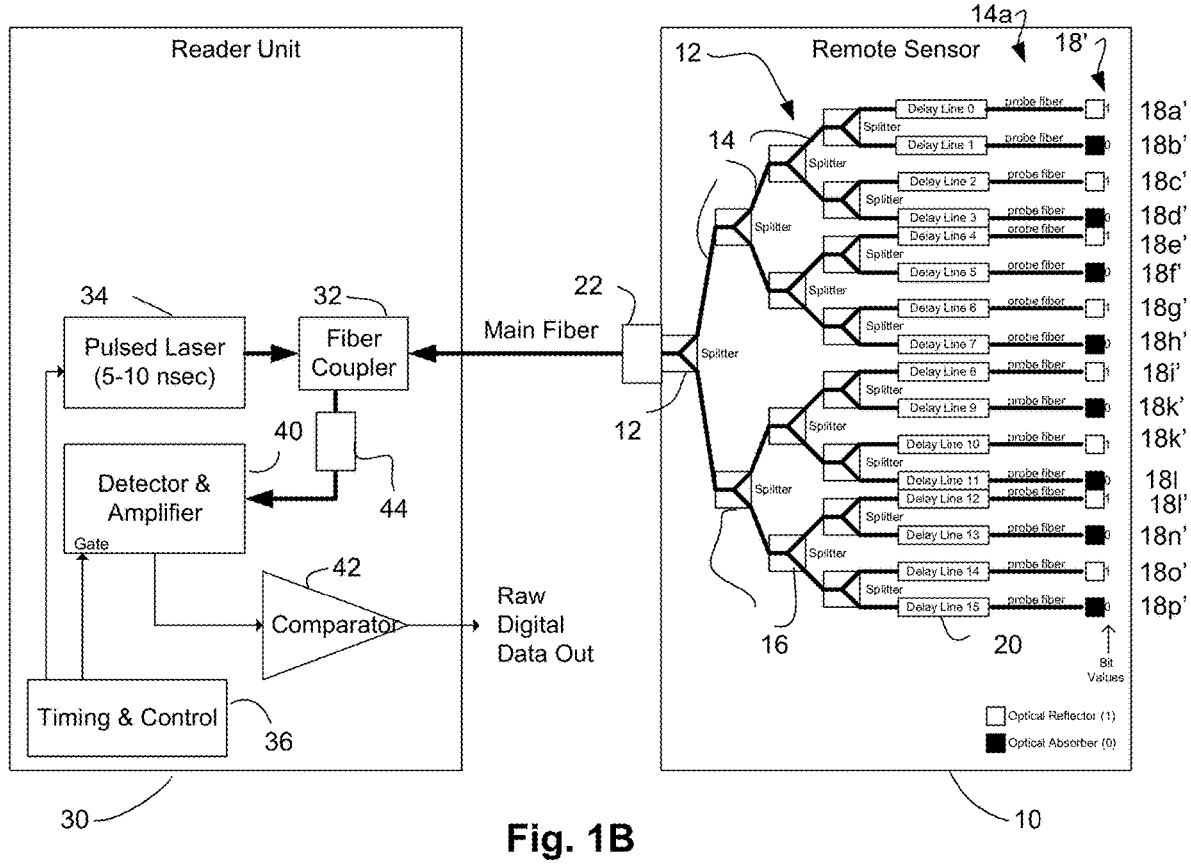
FIG. 1B is a block diagram of an exemplary optical storage device coupled to an interrogator in accordance another embodiment of the present disclosure.

As an alternative to determining the data values based on the reflection or lack of reflection of light, polarization properties of the light can be used to detect the value of each bit. FIG. 1B illustrates such embodiment, which is similar to the embodiment of FIG. 1A and therefore only the differences are discussed here. More particularly, the embodiment of FIG. 1B includes a first polarization filter 22 (either a linear or circular filter) is arranged optically between the interrogator 30 and the first splitter 12 of the optical storage device 10. The first polarization filter 22 is configured to polarize the light prior to passing through the optical waveguides 14. The optical waveguides 14, which in this embodiment would have polarization-maintaining properties such that light passing through the waveguides 14 maintain its polarization, guide the polarized light to optical elements 18' (18a'-18p' in the present example). The optical elements 18', for example, may be in the form of either a metal film reflector (which maintains polarization) or a white paint reflector (which randomizes polarization). The interrogator 30 may include a second polarization filter 44 arranged optically between the coupler 32 and detector and amplifier 40, the filter 44 rotated relative to the first polarization filter 22 so that light pulses from the metal film terminations (maintaining polarization) would be attenuated and be low amplitude (0) while those from the white paint termination would be high amplitude (1) and unpolarized. Another variation of this concept can use polarizers embedded in individual fiber "bits" to filter out or pass through polarized light, with each one using a reflector but potentially different polarizers. An advantage of the polarizer approach is that it can produce a larger difference between the amplitudes of the high amplitude and low amplitude bits.

In accordance with another embodiment of the present disclosure, a single waveguide may be used to store multiple bits of data. For example, an optical storage device can include an optical waveguide, and a plurality of optical elements arranged within the optical waveguide. Each optical element, which may be an FBG, is spaced apart from other optical elements and configured to reflect light (or not reflect light) at a prescribed wavelength, wherein the prescribed wavelength for each respective optical element is different from one another.

Consider, for example, a simple system where a string of Fiber Bragg Gratings (FBG) arranged within a single waveguide are illuminated by a light source and their resulting reflected spectrum is captured by a photo-detector. In this case, each FBG represents a single "digit" of information. By creating the FBGs such that each reflects a different peak wavelength, they can be wavelength division multiplexed (WDM). By this technique, the wavelength spectrum of the illumination source can be divided across the FBGs. The number of available digits is therefore determined by the wavelength resolution of the photo-detector device used to interrogate these FBGs, the line width (or Q) of the FBG, and the bandwidth of the light source.

Figure 3:
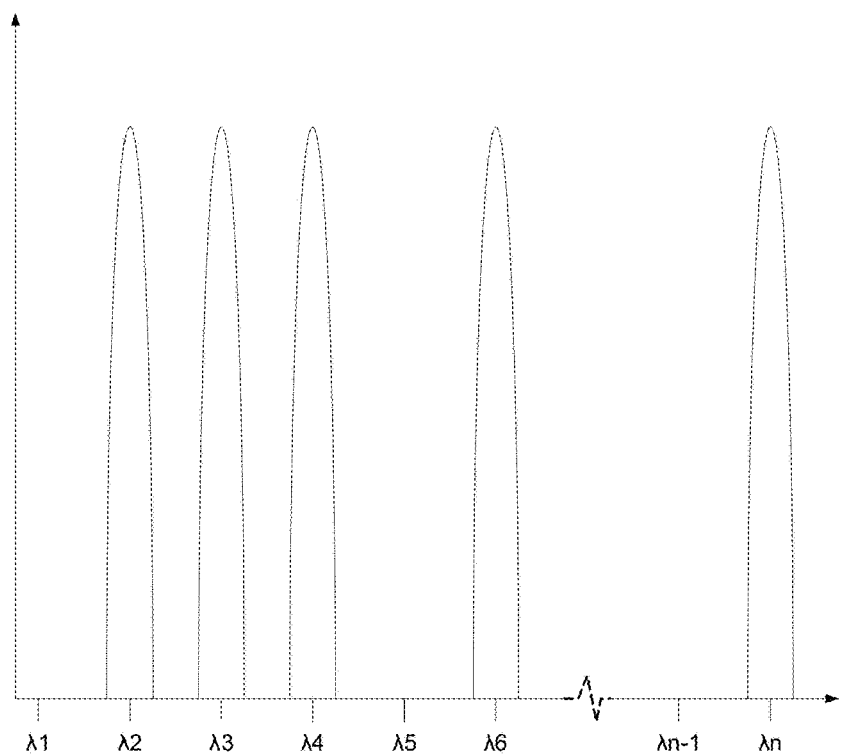
FIG. 3 is a graph representing an amplitude-wavelength domain for FBGs, where each FBG provides a reflection in one band.

For example, and with reference to FIG. 3, the amplitude-wavelength domain for such an array is illustrated. The wavelength spectrum is divided into n wavelength slots, labelled λ1 to λn. It can be seen that if enough spacing is provided between peak wavelengths, the array can represent a series of binary digits. In this case, the resulting number would be 011101 . . . 01. The resulting data will therefore be of size $2^n$ bits.

Figure 4:
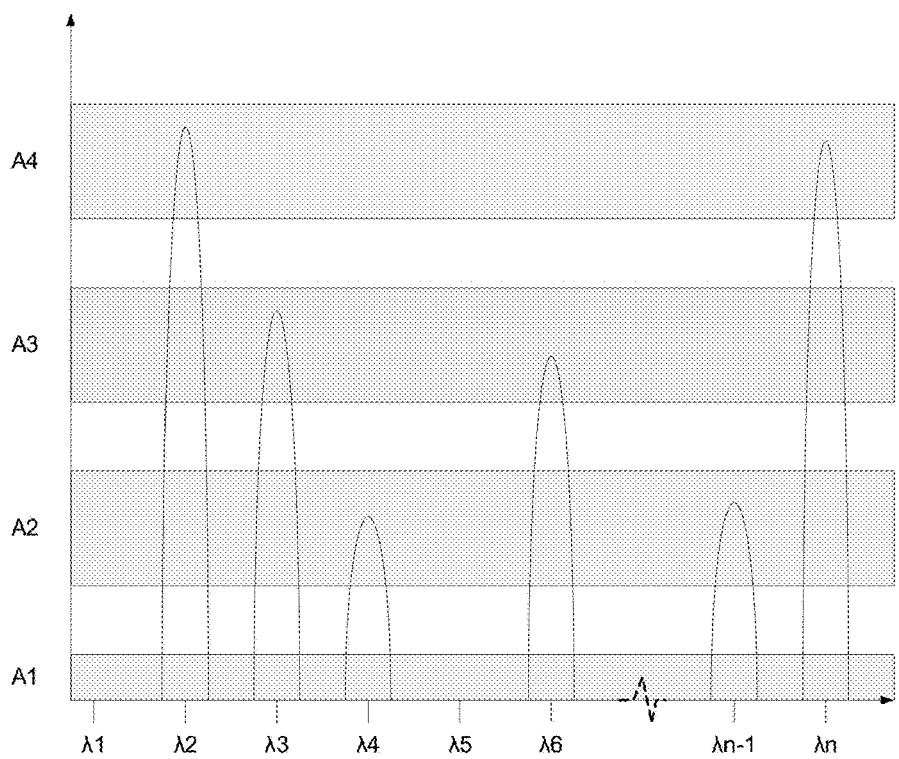
FIG. 4 is a graph representing an amplitude-wavelength domain for FBGs, where each FBG provides a reflection in one of four bands.

Now consider that each FBG can be manufactured to provide partial reflections. FIG. 4 shows an array where each FBG could provide a reflection in one of 4 bands, A1 to A4. Thus this number represents 043203 . . . 24. Accordingly, the amount of data which can be stored is increased now to $4^n$ bits. The number of different amplitude bands which can be used is a function of the stability of the light source, the line width of the FBGs, and the wavelength resolution of the photo-detector.

To interrogate the FBGs, the interrogator 30 can simply transit a laser pulse having a first predetermined wavelength and duration, and then monitor for a response at the predetermined wavelength. If a response is not received, this can be regarded as a value of zero, while if a response is received, then this can be regarded as a value of one. The interrogator 30 then can transmit a second laser pulse at a second predetermined wavelength, and the process repeats until all wavelengths of interest have been analyzed. The collection of responses then can be assembled into a data word for further professing. Optionally, the interrogation system could use a broadband light source with a bandwidth that spans the full wavelength range of the FBGs. Further, the light source can be a scanning laser light source with a bandwidth spans the full wavelength range of the FBGs.

Further, and as noted above with respect to FIG. 4, the amplitude of each response can be analyzed to provide additional data. Thus, if the response for a particular wavelength has an amplitude that is 100% of the transmit pulse, this can be regarded as a value of 4, while a response that has an amplitude that is 25% of the transmit pulse can be regarded as a value of 1 (50% and 75% amplitudes can be regarded as having values of 2 and 3, respectively). As will be appreciated, the amount of data stored per FBG is limited only by the resolution of the laser light source and the photo detector.

In order to protect against drift in light source intensity or any degradation in the FBGs or photo detector, the first FBG could be used as a reference wavelength, based upon which all other FBG responses can be measured. This will also account for any temperature changes or manufacturing tolerances for the optical storage device.

For example, it may be known that a first FBG should reflect light at a particular wavelength and have a particular amplitude (e.g., 100% of the transmit pulse amplitude). During operation, a measurement can be made for the wavelength and/or amplitude of the light reflected by the first FBG. The measured wavelength and/or amplitude then can be compared to the expected wavelength and/or amplitude to determine a "drift" or "offset" value. Thus, for example, if the actual wavelength is 15 nanometers lower than the expected wavelength, then this offset value is added to the measured wavelength for all subsequent FBG measurements. Similarly, if the amplitude is five percent lower than expected, then all other amplitude measurements can be corrected by five percent. In this manner, the system can not only compensate for drift due to temperature variations, but also for a degradation in the light source, FBG and/or the photo detector over time.

Another means of increasing the data density of the FBG array include varying the delay time (via physical distance between a reference FBG and a "target" FBG). This delay time modulation would be an additional independent variable and may require additional optoelectronics for measuring the small time differences involved. It would also require longer waveguide lengths than the other data encoding techniques.

FIG. 5 illustrates an optical storage device 100 in accordance with the second embodiment of the present disclosure. Unlike the optical storage device 10 of FIG. 1, the optical storage device 100 of FIG. 5 uses a single waveguide 102 to store multiple values. More particularly, and as noted above, a plurality of FBGs 104 are arranged serially within the optical waveguide 102 and spaced apart within the waveguide 102 at predetermined intervals. Each FBG 104, which may be etched into the waveguide, is configured to reflect light at a specific peak wavelength and allow other light to pass unimpeded.

The FBGs 104 may be packaged in many ways. In one embodiment, the FBGs are arranged in a waveguide having a linear form factor. While such device is simple to manufacture, a problem with this approach is that the length of the waveguide may require an overly large housing to accommodate the storage device. To minimize the required space, it may be desirable to compact the waveguide. For example, and as shown in FIG. 5, the waveguide 102 can be arranged in a coil configuration, where the waveguide 102 is wrapped around a central core 106. The core 106 can be formed from a light, non-conductive material such as acetal. The waveguide 102 contains FBGs 104 at regular intervals, and a spacing of these regions is defined by the technique used to create the FBGs on the waveguide and could be on the order of 10 cm to 100 cm. Thus, techniques to minimize the overall volume of the packaging such as coiling the waveguide are preferably for a practical solution.

In one embodiment the optical waveguide 102 is an optical fiber. In an alternative embodiment, the optical waveguide 102 may be a solid optical media (such as a glass or plastic) where waveguides and Bragg Gratings are fabricated via the use of femtosecond lasers. Such embodiment can produce a thin, two-dimensional assembly or a thicker three-dimensional assembly containing a large number of interconnected Bragg Gratings and other integrated optical components. Such an assembly would be smaller and more rugged than using a conventional optical fiber.

If the interrogator 30 must interrogate multiple sensors, a single laser and receiver can still be used, as long as each sensor has a unique main fiber length that's a multiple of the time required to read all n bits (160 nanoseconds in the above example). This multi-sensor unit may require a higher-power laser and split it into several transmitting fibers (one for each sensor) using fiber optic splitters. Each transmitting fiber may also need a delay line to provide the required unique main delay value. Optionally, each sensor could be addressed serially using optical switches or an optical switch array.

FIGS. 6 and 7 illustrate an exemplary use case for the optical storage device 100 in accordance with the present disclosure. While FIGS. 6 and 7 illustrate use of the optical storage device 100 shown in FIG. 5, it will be appreciated that the configurations shown in FIGS. 6 and 7 are also applicable to the other embodiments described herein.

In use, the optical storage device 100 can be packaged in the same housing as the sensor 110. FIG. 6 illustrates a first connection methodology, where a single optical waveguide 38 is used to communicate to both the optical storage device 100 and the sensor 110. The sensor 110 may be any optical sensor, but is shown here as a Fabry Perot cavity device with multiple cavities. The optical storage device 100 may be housed in a back portion of the sensor packaging, and can be connected via a single optical waveguide 38 (e.g., an optical fiber) to the interrogator 30. The interrogator 30 houses a single light source 34 and photo-detector 40.

An advantage of the arrangement in FIG. 6 is that only a single waveguide 38 is required to communicate to both the optical storage device 100 and the sensor 110. Also, the interrogator 30 requires only one light source and one photodetector, thereby reducing hardware costs.

A potential drawback, however, is that signals from the respective devices may affect the spectrum of the other, and it may be difficult to distinguish which signal is coming from which device. To prevent the signals from the respective devices from unduly affecting the spectrum of the other, the optical storage device 100 and the optical sensing structures, e.g. Fabry Perot cavities, of the sensor 110 should be manufactured in such a way as to ensure that the optical spectra do not overlap. In some instances this may not be practical, and therefore it may require the use of a separate light source for the sensor and the optical storage device 100, each operating in different wavelength regions.

FIG. 7 illustrates such configuration, where an interrogator 120, in addition to the light source 34 and photo detector 40, includes a second light source 122 and second photo detector 124. A sensor 126 is configured to have the optical storage device 100 on a separate optical link from the other optical signals of the sensor 126. The optical waveguide 38 optically couples the optical storage device 100 to the light source 34 and photodetector 40, while the optical waveguide 128 optically couples the sensors to the second light source 122 and second photodetector 124. In this manner, the optical signals for retrieving data from the optical storage device 100 and the optical signals for receiving sensor data from the sensor 126 are separate and, thus, there is no possibility of interference between the two.

In yet another embodiment, separate optical waveguides may be used as described above with respect to FIG. 7. However, instead of using two light sources and two photodetectors, a single light source and single photodetector may be used. The single light source and photodetector then can be switched between the two optical waveguides depending on whether calibration data or sensor data is being read.

Since the optical storage device 10, 100 is a passive device without any electrical connections, it is intrinsically safe and thus can be used if various environments, including potentially explosive atmospheres, such as can be found in aircraft fuel tanks. Even if multiple interrogation cycles are used, the low duty cycle of the laser will produce a very small amount of energy transmitted in the waveguide, making this a safe optical system.

For example, if the laser pulse width is 10 nanoseconds and the main waveguide length is 100 feet, the main waveguide delay would be 200 nanoseconds and the overall cycle time for 16 bits (at 10 nanoseconds/bit) would be 360 nanoseconds. If the system ran continuously (an unlikely situation), it would have a duty cycle of 10/360=2.8%. If the peak laser power is 1 mW, the average laser power (CW equivalent) would only be 28 µW and the energy from each laser pulse would be 1 pJ ($1\times10^{-12}$ Joules). Even if the system ran continuously for 1 second, it would still only transmit 2.8 µJ of energy into the waveguide at this level. All active and electrically-powered components would reside in the interrogator, which can be located outside the fuel tank.

In another embodiment in accordance with the present disclosure, wavelength-sensitive terminators could be used to allow additional bits of information to be stored without additional couplers or waveguides. In this case, the interrogator would interrogate the sensor with multiple wavelengths.

As discussed herein, the optical storage device 10, 100 can be used to store data, such as sensor calibration data, in an intrinsically safe manner. Such data may be efficiently stored as 8-16 bits of data. In many situations, 8-16 bits of data is sufficient to store calibration data for a typical optical sensor. However, if the calibration data for the sensor (or other device) cannot be stored using 8-16 bits of data, it can become impractical to fabricate the optical storage device to store significantly more data. To overcome such problem, the actual sensor calibration data may be stored remotely on a more-efficient storage medium (e.g., on a magnetic disk, EPROM, etc.) and retrieved based on an identification value retrieved from the optical storage device.

Figure 8:
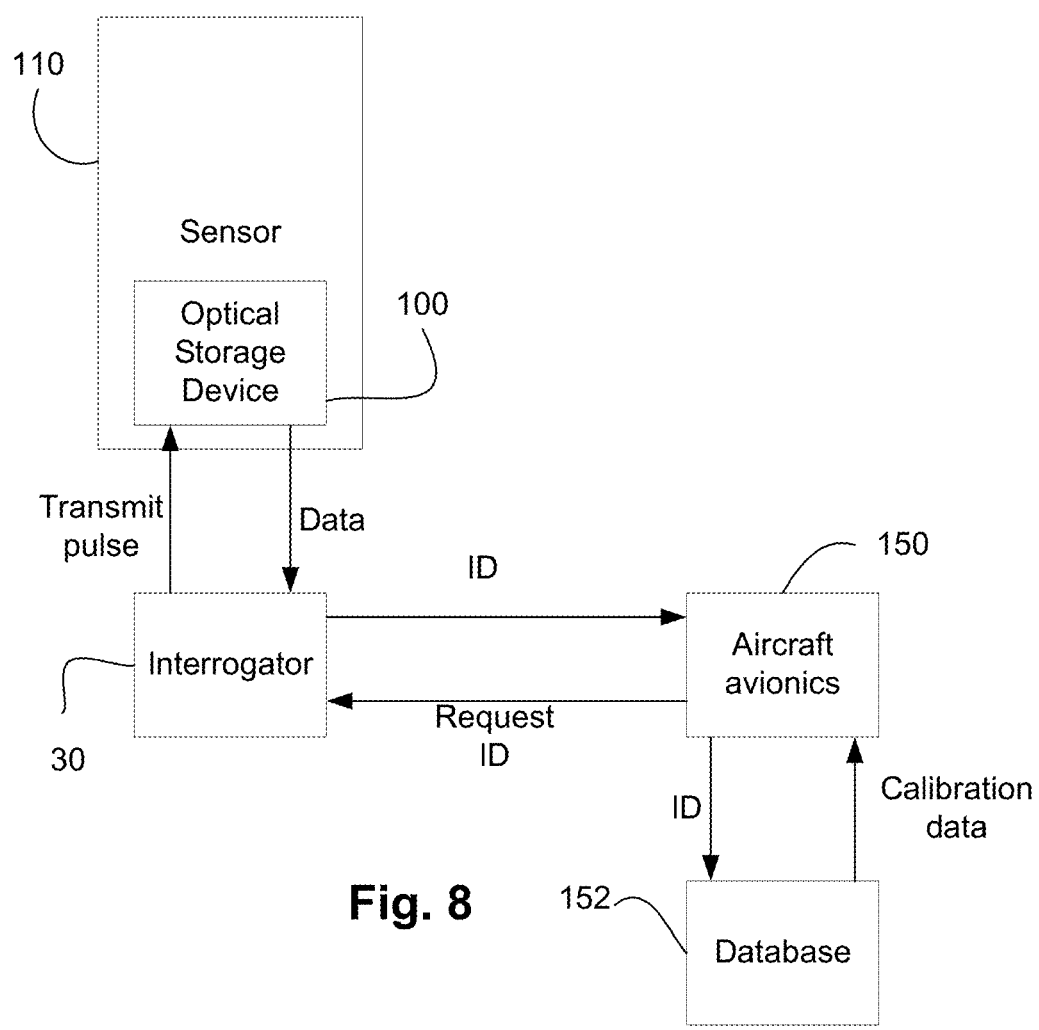
FIG. 8 is a block diagram illustrating a method of retrieving calibration data for a sensor.

For example, and with reference to FIG. 8, an aircraft's avionics system 150 may detect that a sensor 110 has been replaced and thus new calibration data is required. The avionics 150 can send a request to the interrogator 30 to read the data stored in the optical storage device 10, 100. The interrogator outputs one or more transmit pulses to the optical storage device 10, 100 and, in response, the optical storage device 10, 100 provides optical data to the interrogator 30. The interrogator 30 decodes the data from the optical storage device 10, 100, which in the present example is in the form of an identification number (ID), such as, for example, a number between 0 and 255. The interrogator 30 provides the ID number to the avionics system 150, which then accesses a database 152 and requests calibration data associated with the retrieved ID number. The database 152, which may be located remote from the sensor (e.g., in the avionics room) provides the calibration data to the avionics system 150, which then associates the data to the specific sensor. All subsequent data then provided by the sensor 110 is conditioned based on the retrieved calibration data.

Figure 9:
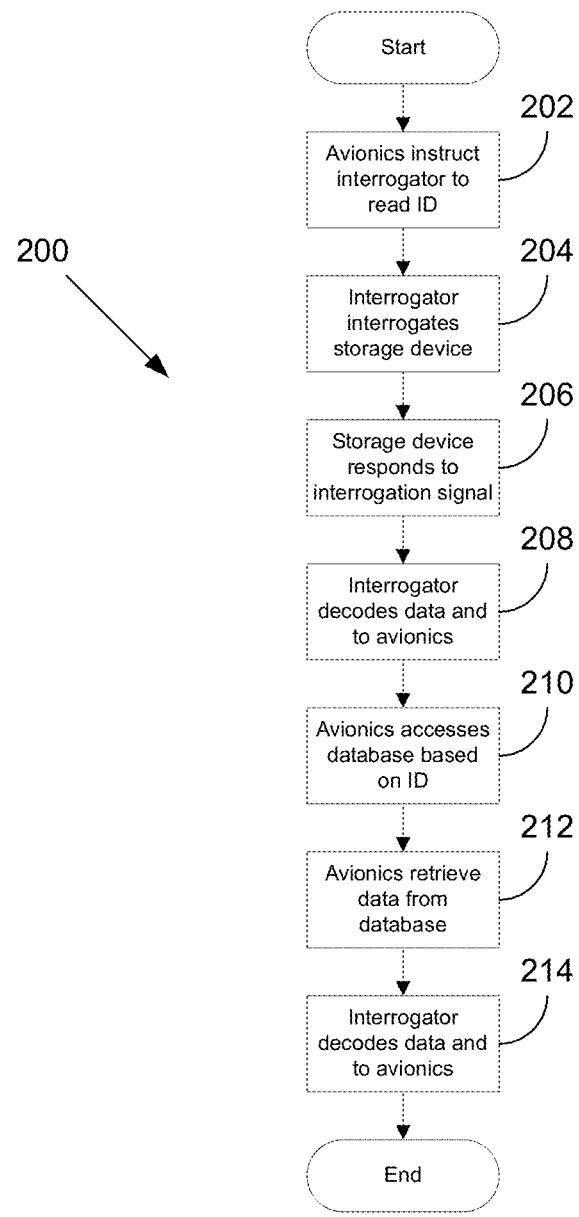
FIG. 9 is a flowchart showing exemplary steps of a method for retrieving data from an optical storage device.

FIG. 9 illustrates exemplary steps 200 for carrying out the method illustrated in FIG. 8. Beginning at step 202, the aircraft avionics 150 instructs the interrogator 30 to read the identifier (e.g., serial number, node address, or other means for identifying the sensor/optical storage device) of the optical storage device 10, 100 and/or sensor 110, 126. At step 204 the interrogator 30 proceeds to read the data stored on the optical storage device 10, 100, for example, by transmitting an optical interrogation signal to the optical storage device 10, 100 as described herein. In response to the interrogation signal, the optical storage device 10, 100 provides optical data to the interrogator as shown at step 206. The optical data then is decoded, for example, by the interrogator 30 and provided to the avionics 150 as shown in step 208. Alternatively, the interrogator 30 may provide the raw optical data to the avionics 150, which then can perform the decoding process.

At step 210 the avionics 150 access a database 152, which may be local or remote from the avionics 150. In accessing the database 152, the avionics requests data (e.g., calibration data) from the database 152 that corresponds to the decoded ID number. For example, the database 152 may include data for ten different sensors, the sensors having ID numbers from 1 to 10, respectively, where the ID number corresponds to data for a particular sensor. If the avionics 150 wishes to retrieve data for a sensor having an ID of 5, the avionics 150 requests that the database 152 provide data that is associated with the ID number 5 as indicated at step 212. The database 152 then retrieves all data that is associated with the ID number of 5 and forwards it to the avionics 150. Once the avionics 150 acquires the data, it applies the data to sensor data provided by the sensor 10, 100. For example, the avionics 150 may scale data provided by the sensor 10, 100 based on the calibration data retrieved from the database 152.

Accordingly, by storing an ID number in the optical storage device 10, 100 and the specific calibration data remote from the sensor, a substantial amount of calibration data can be easily retrieved and associated to a particular sensor data using a minimal amount of optically-stored data. Optionally, the interrogator itself could store the calibration data locally.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An optical storage device for storing data, comprising:
   at least one optical waveguide for receiving an optical interrogation signal and providing a response to the optical interrogation signal; and
   a plurality of optical elements arranged relative to the at least one optical waveguide and responsive to the optical interrogation signal provided through the at least one waveguide to return a prescribed data value through the at least one optical waveguide, wherein each optical element of the plurality of optical elements represents a respective bit of a data word having a predefined value and concerning a function of a sensor.

2. The optical storage device according to claim 1, comprising:
   an interrogation port for interrogating the optical storage device;
   a plurality of optical waveguides optically coupled to the interrogation port, each optical waveguide of the plurality of optical waveguides including a delay element operative to delay the transmission of optical data through a portion of the respective optical waveguide, wherein
   respective ones of the plurality of optical elements terminate respective ones of the plurality of optical waveguides in a prescribed arrangement to form a data sequence.

3. The optical storage device according to claim 2, wherein the optical elements comprise i) optical reflectors and optical absorbers, or ii) polarization changing elements.

4. An optical storage device for storing data, comprising:
   at least one optical waveguide for receiving an optical interrogation signal and providing a response to the optical interrogation signal;
   a plurality of optical elements arranged relative to the at least one optical waveguide and responsive to the optical interrogation signal provided through the at least one waveguide to return a prescribed data value through the at least one optical waveguide, wherein the plurality of optical elements represent encoded data concerning a function of a sensor;
   an interrogation port for interrogating the optical storage device; and a plurality of optical waveguides optically coupled to the interrogation port, each optical waveguide of the plurality of optical waveguides including a delay element operative to delay the transmission of optical data through a portion of the respective optical waveguide, wherein respective ones of the plurality of optical elements terminate respective ones of the plurality of optical waveguides in a prescribed arrangement to form a data sequence, and wherein the delay introduced by each respective delay element of the plurality of delay elements is different from other delay elements of the plurality of delay elements.

5. An optical storage device for storing data, comprising:

at least one optical waveguide for receiving an optical interrogation signal and providing a response to the optical interrogation signal;

a plurality of optical elements arranged relative to the at least one optical waveguide and responsive to the optical interrogation signal provided through the at least one waveguide to return a prescribed data value through the at least one optical waveguide, wherein the plurality of optical elements represent encoded data concerning a function of a sensor;

an interrogation port for interrogating the optical storage device; and a plurality of optical waveguides optically coupled to the interrogation port, each optical waveguide of the plurality of optical waveguides including a delay element operative to delay the transmission of optical data through a portion of the respective optical waveguide, wherein respective ones of the plurality of optical elements terminate respective ones of the plurality of optical waveguides in a prescribed arrangement to form a data sequence, and wherein each delay element of the plurality of delay elements is arranged optically between the interrogation port and the respective optical element.

6. The optical storage device according to claim 2, further comprising at least one optical splitter having an input port and a plurality of output ports, wherein the input port is coupled to the interrogation port and respective ones of the plurality of optical waveguides are coupled to respective ones of the plurality of output ports.

7. The optical storage device according to claim 1, wherein the plurality of optical elements are arranged within the at least one optical waveguide, each optical element of the plurality of optical elements spaced apart from other optical elements of the plurality of optical elements and configured to reflect light at a prescribed wavelength, wherein the prescribed wavelength for each respective optical element of the plurality of optical elements is different from one another.

8. The optical storage device according to claim 7, wherein the array of optical elements comprises a plurality of Fiber Bragg Gratings (FBG) arranged serially in the optical fiber.

9. The optical storage device according to claim 7, wherein the optical waveguide is arranged in a coil configuration.

10. The optical element according to claim 7, wherein the optical waveguide is wrapped around a central core to produce a coil-shape optical waveguide.

11. The optical element according to claim 10, wherein the central core comprises a non-conductive material.

12. The optical storage device according to claim 7, wherein the plurality of optical elements are written within the optical waveguide.

13. The optical storage device according to claim 7, wherein the spacing between adjacent optical elements is between 10 centimeters and 100 centimeters.

14. The optical storage device according to claim 1, wherein the plurality of optical elements are configured to provide partial reflections of the optical interrogation signal.

15. The optical storage device according to claim 14, wherein the partial reflections comprise n different bands, where n is an integer greater than 1.

16. The optical storage device according to claim 1, wherein the optical waveguide comprises an optical fiber.

17. An optical sensor system, comprising:

an optical sensor; and the optical storage device according to claim 1.

18. The optical sensor system according to claim 17, further comprising an interrogator communicatively coupled to the optical sensor via a first optical medium, and communicatively coupled to the optical storage device via a second optical medium.

19. The optical sensor system according to claim 18, wherein the first optical medium and the second optical medium are different from one another.

20. The optical sensor system according to claim 17, wherein the interrogator is configured to decode data received from the optical storage device based on time division multiplexing and time of flight calculations.

21. The optical sensor system according to claim 17, wherein the interrogator is configured to decode data received from the optical storage device based on one of time division multiplexing or wavelength division multiplexing.

22. The optical storage device according to claim 1, wherein the at least one optical waveguide comprises a plurality of optical waveguides, and each optical element of the plurality of optical elements is arranged relative to a respective one of the plurality of optical waveguides and is responsive to the optical interrogation signal provided through the respective optical waveguide to return a prescribed data value through the respective optical waveguide.

* * * * *